(12) United States Patent
Kitabatake et al.

(10) Patent No.: US 6,667,292 B1
(45) Date of Patent: Dec. 23, 2003

(54) NITRIC MONOXIDE METABOLITE-POLYOXYALKYLENE-HEMOGLOBIN COMPLEX

(75) Inventors: Akira Kitabatake, Hokkaido (JP); Ichiro Sakuma, Hokkaido (JP); Kunihiko Nakai, Miyagi (JP); Tohru Yasukohchi, Kanagawa (JP)

(73) Assignees: Hokkaido University, Hokkaido (JP); NOF Corporation, Tokyo (JP)

( * ) Notice: Subject to any disclaimer, the term of this patent is extended or adjusted under 35 U.S.C. 154(b) by 0 days.

(21) Appl. No.: 09/499,758

(22) Filed: Feb. 8, 2000

(30) Foreign Application Priority Data

Feb. 8, 1999 (JP) ............................................ 11-067239

(51) Int. Cl.⁷ ....................... A61K 35/14; C07K 14/805
(52) U.S. Cl. ......................................... 514/21; 530/385
(58) Field of Search ............................. 530/385; 514/21

(56) References Cited

U.S. PATENT DOCUMENTS

| | | | | |
|---|---|---|---|---|
| 4,301,144 A | * | 11/1981 | Iwashita et al. | ............... 424/78 |
| 4,412,989 A | * | 11/1983 | Iwashita et al. | ............. 424/177 |
| 5,804,561 A | * | 9/1998 | Hsia | ............. 514/21 |

FOREIGN PATENT DOCUMENTS

| | | |
|---|---|---|
| EP | 0 206 448 A1 | 12/1986 |
| JP | B-5-64128 | 9/1993 |
| JP | B6-76333 | 9/1994 |
| WO | WO 95/05397 | 2/1995 |
| WO | WO 96/29974 | 10/1996 |
| WO | WO 96/30006 | * 10/1996 |
| WO | WO 97/18000 | 5/1997 |
| WO | WO 98/34955 | 8/1998 |

OTHER PUBLICATIONS

The Renal Handling of Hemoglobin, I. Glomular Filtration, H. Franklin Bunn, M.D., William T. Esham, and Robert W. Bull, D.V.M., Published Jan. 6, 1969, pp. 909–924.

Evaluation of a Stroma–Free Hemoglobin Solution for Use as a Plasma Expander, S. Frederick Rabiner, M.D., J. Raymond Helbert, PhD., Harry Lopas, M.D., and Lila H. Friedman, Published Jul. 17, 1967, pp. 1127–1142.

Transfusion Medicine Reviews, "Hemoglobin–Nitric Oxide Interaction and Its Implications", Roberto Motterlini, Kim D. Vandegriff, and Robert M. Winslow, vol. X, No. 2, 4/96, pp. 77–84.

Permeability Characteristics of Hemoglobin Derivatives Across Cultrued Endothelial Cell Monolayers, Kunihiko Nakai, Ichiro Sakuma, Toshio Ohta, Joji Ando, Akira Kitabatake, Yoshikazu Nakazato, and Tsuneo A. Takahashi, J. Lab. Clin. Med. 132(4), 10/98, pp. 312–319.

The Effects of Recombinant Human Hemoglobin on Esophageal Motor Function in Humans, Joseph A. Murray, Amber Ledlow, Janice Launspach, Donna Evans, Michelle Loveday, and Jeffrey L. Conklin, Gastroenterology 1995, vol. 109, No. 4, pp. 1241–1248.

Experimental Medicine, vol. 9, No. 11, pp. 1347–1351 (1991).

* cited by examiner

Primary Examiner—Brenda Brumback
Assistant Examiner—Anish Gupta
(74) Attorney, Agent, or Firm—Sughrue Mion, PLLC

(57) ABSTRACT

Disclosed is a nitric monoxide metabolite-polyoxyalkylene-hemoglobin complex having a molecular weight of from 100,000 to 2,000,000 daltons, in which a polyoxyalkylene derivative is bound to from 10 to 30% in total of bindable amino groups in hemoglobin and a nitric monoxide metabolite is bound to from 10 to 100% in total of thiol groups of cysteine residues.

9 Claims, 2 Drawing Sheets

RETENTION TIME (MIN.)

NITRITE MEASUREMENT BY GRIESS' REAGENT

UNMODIFIED HEMOGLOBIN

RETENTION TIME (MIN.)

RETENTION TIME (MIN.)

NITRIC MONOXIDE METABOLITE-POLYOXYALKYLENE-HEMOGLOBIN COMPLEX

BACKGROUND OF THE INVENTION

1. Field of the Invention

This invention relates to a nitric monoxide metabolite-polyoxyalkylene-hemoglobin complex which is useful in blood substitutes and organ perfusion solutions, a method for the production of said complex and an oxygen carrier solution which contains said complex, more particularly to a cell-free hemoglobin-based oxygen carrier which has high safety in blood and does not cause problems such as hypertension (blood pressure increase) at the time of injection into the living body.

2. Background Art

Currently, attempts are made positively to use cell-free hemoglobin extracted from human or bovine erythrocytes as an oxygen carrier substitute of erythrocyte blood transfusion.

It is necessary to solve various problems in order to use cell-free hemoglobin directly as an oxygen carrier substitute for erythrocyte blood transfusion. Firstly, stroma as a membrane fragment remains in erythrocyte hemolysate and causes blood coagulation. In this field, Rabiner et al. have established in 1967 a method for the production of stroma-free hemoglobin in which stroma is removed from a hemoglobin solution (Rabiner S. F. et al., Evaluation of a stroma-free hemoglobin solution for use as a plasma expander, *J. Exp. Med.*, 126, 1127–1142, 1967), which solved the problem of disseminated intravascular coagulation (DIC) almost completely. Next, hemoglobin molecules are leaked from the renal glomerulus and exert toxicity upon the renal tube. The problem of renal toxicity has also been solved almost completely based on the finding by Bunn et al. in 1969 that excretion of hemoglobin from the glomerulus can be avoided by introducing intramolecular crosslinking into hemoglobin (Bunn F. et al., The renal handling of hemoglobin, *J. Exp. Med.*, 129, 909–924, 1969) and the subsequent finding that excretion of hemoglobin into urine can be prevented and its intravascular half life can be prolonged by increasing molecular weight of hemoglobin through its chemical modification with polyethylene glycol (e.g., JP-B-5-64128 and JP-B-6-76333; the term "JP-B" as used herein means an "examined Japanese patent publication"). Based on these technical improvement, studies on the cell-free hemoglobin as an erythrocyte substitution oxygen carrier have been advanced, and several products are already entering into clinical tests in the United States.

However, as the studies on such hemoglobin derivatives progressed, two new problems have been found. That is, blood pressure increasing reaction accompanied by vasoconstriction and abdominal pain accompanied by intestinal constriction.

It is considered that the main cause of the blood pressure increasing reaction as the first problem is vasoconstriction, particularly of the arteriole, induced by the administration of hemoglobin derivatives. This phenomenon is considered to be undesirable, because it is not recognized when normal erythrocyte transfusion is carried out, and constriction of the arteriole inhibits the flow of blood into capillary vessels where transfer of oxygen is carried out. It is considered that this vasoconstriction occurs due to the reaction of an endothelium-derived relaxing factor [EDRF: considered to be nitric monoxide or a nitric monoxide releasing substance (I. Sakuma, NO as a blood vessel relaxing factor, *Experimental Chemistry*, 9, 1347–1351, 1991)] with cell-free hemoglobin, which causes elimination of EDRF and thereby entails constriction of blood vessels (Motterlini R. et al., Hemoglobin-nitric oxide interaction and its implications, *Transfusion Med. Rev.*, 10, 77–84, 1996). Particularly, it is important that EDRF is disappeared inside the blood vessel wall by the incorporation of hemoglobin molecules into the vessel through endothelium gaps (Nakai K. et al., Permeability characteristics of hemoglobin derivatives across cultured endothelial cell monolayers, *J. Lab. Clin. Med.*, 132, 313–319, 1998).

Next, with the commencement of clinical tests in the human body in recent years, intestinal constriction caused by cell-free hemoglobin derivatives has been drawing attention as a new problem. Though its cause is not specified yet, this phenomenon is observed mostly in clinical tests of intramolecular crosslinking type hemoglobin, and it is assumed that its cause is the elimination of nitric monoxide as a candidate of anti-adrenergic anti-cholinergic neurotransmitter, also caused by the cell-free hemoglobin leaked for example from the endothelium (Murray J. A. et al., The effects of recombinant human hemoglobin on esophageal motor functions in humans, *Gastroenterology*, 109, 1241–1248, 1995).

Since the elimination of nitric monoxide by hemoglobin is the cause of each of these side effects, it has been proposed that it is effective to use a nitric monoxide metabolite-bonded hemoglobin to which transferring and releasing abilities of the nitric monoxide metabolite are added (Stamler, WO 96/30006). The nitric monoxide metabolite-bonded hemoglobin is a modified form of hemoglobin in which a nitric monoxide metabolite is reversibly bound to the β-chain cysteine residue of hemoglobin, which can release the nitric monoxide metabolite having a physiological activity by compensating the elimination of nitric monoxide by the heme of hemoglobin. However, since this nitric monoxide metabolite-bonded hemoglobin is an intramolecular crosslinking type hemoglobin having small molecular weight, it still has a problem in that its half life in blood vessels is short due to its aptness to be excreted into urine.

Thus, the modified forms of hemoglobin are markedly promising as oxygen carriers for use, for example, in erythrocyte substitution blood transfusion and organ perfusion solution, but, as described in the foregoing, nothing has been proposed yet on their counterpart which is not easily be excreted, has therefore a long half life in the body and shows no side effects such as vasoconstriction and intestinal constriction.

Accordingly, great concern has been directed toward the development of a cell-free hemoglobin derivative which can be used safely and freely and is storable for a prolonged period of time.

SUMMARY OF THE INVENTION

An object of the present invention is to provide an oxygen carrier capable of being used safely and freely and being stored for a prolonged period of time, whose leakage from the renal glomerulus and vascular endothelium is extremely limited and which has a nitric monoxide metabolite releasing ability that can compensate removal of endothelium-derived nitric monoxide. Another object of the present invention is to provide an oxygen carrier solution which contains a specified amount of the nitric monoxide metabolite-polyoxyalkylene-hemoglobin complex (to be referred sometimes to as "modified compound" hereinafter) of the present invention. Since the oxygen carrier solution can be prepared simply and easily, it is useful as an erythrocyte substitution blood transfusion or organ perfusion solution.

The inventors of the present invention have conducted intensive studies on an oxygen carrier which can be used safely and freely causing no side effects such as renal toxicity, hypertension and abdominal pain and found as a result of the efforts that a derivative having a molecular weight of from 100,000 to 2,000,000, prepared by binding a specified polyoxyalkylene derivative and a nitric monoxide metabolite to cell-free hemoglobin extracted from human or bovine erythrocytes, is a markedly promising oxygen carrier, thus resulting in the accomplishment of this invention.

Accordingly, an object of the present invention is to provide a nitric monoxide metabolite-polyoxyalkylene-hemoglobin complex (modified compound) having a molecular weight of from 100,000 to 2,000,000 daltons, in which a polyoxyalkylene derivative is bound to from 10 to 30% in total of bindable amino groups in hemoglobin and a nitric monoxide metabolite is bound to from 10 to 100% in total of thiol groups of cysteine residues.

More particularly, it is the just described nitric monoxide metabolite-polyoxyalkylene-hemoglobin complex, wherein it uses a polyoxyalkylene derivative of formula (1):

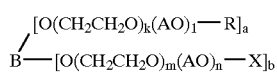
(1)

wherein B represents residue of a compound having from 2 to 6 hydroxyl groups, AO represents an oxyalkylene group having 3 or 4 carbon atoms, R represents a hydrocarbon group having from 1 to 30 carbon atoms or a hydroxyl group, k and m are numbers which satisfy $0 \leq k \leq 500$ and $0 \leq m \leq 500$, respectively, and also $20 \leq k+m \leq 1000$, as the average addition mol number of oxyethylene groups, l and n are numbers which satisfy $0 \leq l \leq 10$ and $0 \leq n \leq 10$, respectively, and also $0 \leq l+n \leq 10$, as the average addition mol number of oxyalkylene groups, a and b are numbers which satisfy $0 \leq a \leq 6$ and $1 \leq b \leq 6$, respectively, and also $2 \leq a+b \leq 6$, and X represents a functional group capable of binding to the amino group shown by formula (2), (3), (4) or (5);

$$-(CH_2)_c-COOY \qquad (2)$$

wherein c is a number of from 0 to 2 and Y represents hydrogen or p-nitrophenyl group or N-hydroxysuccinimide residue, $$-OC-(CH_2)_d-COOY \qquad (3)$$

wherein d is a number of from 2 to 6 and Y represents hydrogen or N-hydroxysuccinimide residue, $$-(CH_2)_e-CHO \qquad (4)$$

wherein e is 1 or 2, and $$-COZ \qquad (5)$$

wherein Z represents imidazole group.

Another object of the present invention is to provide the aforementioned nitric monoxide metabolite-polyoxyalkylene-hemoglobin complex, wherein it uses an s-nitroso-low molecular weight (preferably having 1,000 daltons or less) thiol compound such as s-nitrosoglutathione as the nitric monoxide metabolite.

A further object of the present invention is to provide an oxygen carrier solution which contains the nitric monoxide metabolite-polyoxyalkylene-hemoglobin complex in an amount of from 10 g/L to 200 g/L.

Yet another object of the present invention is to provide a method for producing a nitric monoxide metabolite-polyoxyalkylene-hemoglobin complex having a molecular weight of from 100,000 to 2,000,000 daltons, in which a polyoxyalkylene derivative is bound to from 10 to 30% in total of bindable amino groups in hemoglobin and a nitric monoxide metabolite is bound to from 10 to 100% in total of thiol groups of cysteine residues, which comprises carrying out a one step method, namely, allowing a polyoxyalkylene-hemoglobin complex to react with a nitric monoxide metabolite.

A still further object of the present invention is to provide a method for producing a nitric monoxide metabolite-polyoxyalkylene-hemoglobin complex having a molecular weight of from 100,000 to 2,000,000 daltons, in which a polyoxyalkylene derivative is bound to from 10 to 30% in total of bindable amino groups in hemoglobin and a nitric monoxide metabolite is bound to from 10 to 100% in total of thiol groups of cysteine residues, which comprises carrying out a two step method, namely allowing a polyoxyalkylene-hemoglobin complex to react with a nitric monoxide metabolite and then with a polyoxyalkylene derivative.

DETAILED DESCRIPTION OF THE INVENTION

Figure 1:
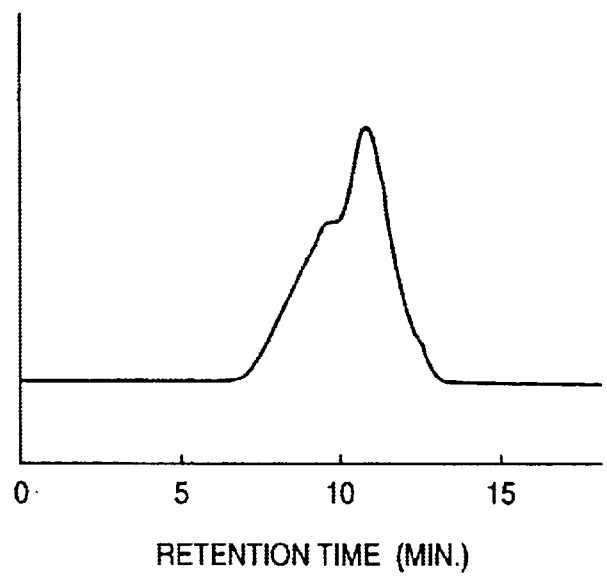
FIG. 1 is a graph showing a result of gel permeation chromatography measurement of the s-nitrosoglutathione-polyoxyethylene-hemoglobin complex obtained in Inventive Example 1 using human erythrocyte hemoglobin.

Regarding the cell-free hemoglobin to be used in the present invention, a human or bovine origin may be used as such or after its intramolecular crosslinking, but it is desirable to use human origin hemoglobin when ethical aspects are taken into consideration, and it is more desirable to use those which are intramolecularly crosslinked with pyridoxal phosphates such as pyridoxal 5'-phosphate and 2-nor-2-formylpyridoxanol 5'-phosphate, pyridoxal sulfates such as pyridoxal 5'-sulfate, glycerol phosphates such as glycerol 2,3-diphosphate or sugar phosphates such as glucose 6-phosphate and adenosine 5'-phosphate.

Also, the number of bindable amino groups (amino groups of lysine residue and N-terminal amino groups) in hemoglobin varies depending on the types of hemoglobin to be used. It is considered that the total number of bindable amino groups in the case of human hemoglobin is 48 including 4 N-terminal amino groups and 44 lysine residue amino groups, and the total number of bindable amino groups in the case of bovine hemoglobin is 50 including 4 N-terminal amino groups and 46 lysine residue amino groups. In addition, it also varies depending on the number of functional groups (b) of the polyoxyalkylene derivative to be used, so that, when the number of polyoxyalkylene derivative molecules to be bound to the amino groups, though it cannot be specified, is too small, molecular weight of the compound of interest cannot be increased to a level sufficient enough to prevent its leakage from cells, and their excess binding is also undesirable, because it requires severe reaction conditions which cause reduction of the oxygen transferring capacity of hemoglobin by destroying its three dimensional structure. Accordingly, the number is limited to a range of from 10 to 30% of the total number of bindable amino groups. Preferred range is from 15 to 25%.

When the number of a nitric monoxide metabolite to be bound to thiol groups of the two bindable cysteine residues existing in hemoglobin is too small, sufficient effect for inhibiting the blood pressure increasing action cannot be obtained. In order to inhibit the blood pressure increasing action, it is necessary to bind the nitric monoxide metabolite to from 10 to 100% in total of thiol groups of cysteine residues.

Examples of the nitric monoxide metabolite which can be used in the present invention include any one of s-nitroso derivatives of low molecular weight (molecular weight: 1,000 daltons or less) thiol compounds, such as N-acetyl-DL-penicillanine, N-acetyl-L-cysteine, s-nitrosocysteine and s-nitrosoglutathione. However, when reactivity and the like are taken into consideration, it is desirable to use s-nitrosoglutathione because of its superior reactivity.

Molecular weight of the nitric monoxide metabolite-polyoxyalkylene-hemoglobin complex to be obtained by the present invention is within the range of from 100,000 to 2,000,000 daltons, because the molecular weight if smaller than 100,000 daltons would cause easy leakage of the complex from endothelium and the like tissues and if larger than 2,000,000 daltons would entail a difficulty in its handling due to too high viscosity.

Its preferred range is from 150,000 to 1,500,000 daltons. In this connection, the molecular weight is peak top molecular weight of the maximum peak.

Also, examples of the residue of compound having from 2 to 6 hydroxyl groups, represented by B in the formula (1), include residues of ethylene glycol, propylene glycol, butylene glycol, glycerol, trimethylolpropane, diglycerol, pentaerythritol, triglycerol, sorbitol and tetraglycerol.

Also, examples of the oxyalkylene group having 3 or 4 carbon atoms, represented by AO, include oxypropylene group, oxyisopropylene group, oxybutylene group and oxyisobutylene group.

Also, examples of the hydrocarbon group having from 1 to 30 carbon atoms, represented by R, include methyl, ethyl, propyl, isopropyl, butyl, isobutyl, pentyl, isopentyl, hexyl, isohexyl, octyl, isooctyl, nonyl, isononyl, decyl, dodecyl, tridecyl, tetradecyl, hexadecyl, octadecyl, octadecenyl, eicosyl, docosyl, tetracosyl, hexacosyl, octacosyl, triacontyl and the like groups, of which, though any of them may be used depending on each purpose, preferred are those which have 1 to 4, more preferably 1 or 2, carbon atoms because when the carbon number is large, a problem such as bubbling tends to occur due to its surfactant ability.

The oxyethylene group is essential for forming a hydrophilic layer on the peripheral of the hemoglobin derivative, and its addition mol number is expressed by k and m, wherein the number if too small would cause frequent leakage of the derivative from the renal glomerulus due to insufficient size of the hydrophilic layer and if too large would entail a difficulty in handling the derivative due to increased viscosity. Accordingly, its range which can be used for the purpose of the present invention is $0 \leq k \leq 500$, $0 \leq m \leq 500$ and also $20 \leq k+m \leq 1000$, preferably $0 \leq k \leq 500$, $0 \leq m \leq 500$ and also $50 \leq k+m \leq 800$.

The oxyalkylene group is introduced for the purpose of increasing stability of the binding site of the polyoxyalkylene derivative and hemoglobin, and the addition mol number of oxyalkylene groups, expressed by l and n, is limited to the range of $0 \leq l \leq 10$, $0 \leq n \leq 10$ and also $0 \leq l+n \leq 10$, because formation of the hydrophilic layer is inhibited when the number is too large. Preferred range is $0 \leq l \leq 4$, $0 \leq n \leq 4$ and also $0 \leq l+n \leq 4$.

Also, a represents the number of polyoxyalkylene chains which cannot bind to hemoglobin, and b represents the number of polyoxyalkylene chains which can bind to hemoglobin. The number b must be at least 1 for effecting binding of hemoglobin and oxyalkylene derivative, and when the number of b is increased to 2 or more, it renders possible efficient increase in the molecular weight of nitric monoxide metabolite-polyoxyalkylene-hemoglobin complex through partial crosslinking of the complex molecules. However, when the number of b is too large, the crosslinking progresses to such a level that gelation and the like problems are apt to occur, so that the preferred range of b is from 1 to 4.

Any optional functional group can be used as X, with the proviso that it can bind to the amino group of lysine residue and N-terminal amino group, but when its reactivity and the like are taken into consideration, it is desirable to use an activated carboxylic acid type represented by the formula (2) or (3), an aldehyde type represented by the formula (4) or an imidazole type represented by the formula (5) The activated carboxylic acid type represented by the formula (2) or (3) is particularly desirable.

The nitric monoxide metabolite-polyoxyalkylene-hemoglobin complex of the present invention can maintain its oxygen carrying ability markedly stably under freeze-dried condition, so that it is possible to preserve it for a prolonged period of time easily and simply and it can be used for example in erythrocyte substitution blood transfusion or organ perfusion by diluting it for example with physiological saline at the time of its practical use. In that case, concentration of the nitric monoxide metabolite-polyoxyalkylene-hemoglobin complex cannot always be specified, because it varies depending on the molecular weight of the nitric monoxide metabolite-polyoxyalkylene-hemoglobin complex to be used and the tructure of polyoxyalkylene derivative incorporated into the nucleus, and also depending on the intended oxygen carrying ability, but it is generally from 10 to 200 g/L, because the concentration when smaller than 10 g/L will entail insufficient oxygen carrying ability of the oxygen carrier solution due to too low concentration of the hemoglobin derivative in the solution and when larger than 200 g/L will cause a difficulty in handling the oxygen carrier solution due to its too high viscosity. It is preferably from 50 to 150 g/L, more preferably from 60 to 120 g/L.

The polyoxyalkylene derivative of formula (1) to be used in the present invention can be obtained for example by the following method.

The compound of general formula (6) having hydroxyl group on its terminal is obtained by carrying out the reaction to add ethylene oxide and, as occasion demands, an alkylene oxide having 3 or 4 carbon atoms to the compound represented by B having from 2 to 6 hydroxyl groups in the usual way using an alkali catalyst such as sodium hydroxide, potassium hydroxide, metallic sodium or sodium methylate, neutralizing the alkali catalyst using a mineral acid such as hydrochloric acid or phosphoric acid, dehydrating the reaction mixture and then removing the thus formed neutralized salt by filtration.

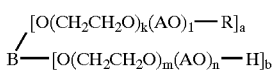 (6)

Next, the terminal hydroxyl group of the thus obtained compound of formula (6) is changed to a functional group capable of binding to amino group, represented by the formula (2), (3), (4) or (5) depending on each purpose.

This reaction can be effected by employing various known methods.

For example, when the terminal hydroxyl group is changed to the group of formula (2), the compound of interest can be obtained by preparing a compound having carboxylic acid on the terminal by employing a method in which the hydroxyl group is allowed to react with a halogenated carboxylic acid such as monochloroacetic acid or monobromoacetic acid in the presence of an alkali catalyst, a method in which the hydroxyl group is allowed to react with acrylonitrile in the presence of an alkali catalyst and then subjected to hydrolysis or a method in which the terminal hydroxyl group is oxidized using hydrogen peroxide, permanganic acid or platinum- or palladium-carbon catalyst, and then making the resulting compound into N-hydroxysuccinimide ester using a dehydrating agent such as dicyclohexylcarbodiimide. In an alternative method, the terminal may be firstly made into a form of acid chloride by allowing it to react with a chloroformate such as phosgene and then allowed to react with N-hydroxysuccinimide. Also, the terminal hydroxyl group may be allowed to react directly with an activated chloroformate such as p-nitrophenyl chloroformate in the presence of a basic catalyst. There are many known methods for these reactions, and any of them can be employed.

Also, when the terminal hydroxyl group is changed to the group of formula (3), the compound of interest can be obtained by preparing a compound having carboxylic acid on the terminal by allowing the terminal hydroxyl group to react with a dibasic acid anhydride such as succinic anhydride or glutaric anhydride, directly or in the presence of a basic catalyst, and then making the resulting compound into an activated ester by allowing it to react with N-hydroxysuccinimide in the presence of a dehydrating agent such as dicyclohexylcarbodiimide.

Also, when the terminal hydroxyl group is changed to the group of formula (4), the compound of interest can be obtained by oxidizing the terminal hydroxyl group in the presence of dimethyl sulfoxide and acetic anhydride or in the presence of potassium permanganate.

Also, when the terminal hydroxyl group is changed to the group of formula (5), the compound of interest can be obtained by allowing the terminal group to react with carbonyldiimidazole in the presence of a basic catalyst.

In order to obtain the nitric monoxide metabolite-polyoxyalkylene-hemoglobin complex of the present invention, a polyoxyalkylene-hemoglobin complex (to be referred, for the sake of convenience, to as "precursor modified compound" hereinafter) is firstly obtained by allowing the compound of formula (1) obtained by the aforementioned method (polyoxyalkylene derivative) to react with hemoglobin.

Next, the nitric monoxide metabolite-polyoxyalkylene-hemoglobin complex (to be referred to as "modified hemoglobin compound of interest" hereinafter) is obtained by allowing the precursor modified compound to react with a nitric monoxide metabolite (e.g., s-nitrosoglutathione) in an amount of from 2 to 10 moles based on 1 mole of hemoglobin used, in a buffer solution having a pH value of from 7 to 10 and at a temperature of from 0 to 40° C.

In this case, unreacted hemoglobin, unreacted polyoxyalkylene derivative, nitric monoxide metabolite and buffer salt are removed using an appropriate ultrafiltration membrane. Thereafter, the product may be freeze-dried to make it into powder as occasion demands.

Alternatively, a polyoxyalkylene-hemoglobin derivative (to be referred to as "preliminary precursor modified compound" hereinafter) is firstly obtained by allowing the polyoxyalkylene derivative of formula (1) to react with hemoglobin, and the nitric monoxide metabolite-polyoxyalkylene-hemoglobin complex (modified hemoglobin compound of interest) is obtained by allowing the preliminary precursor modified compound to react with a nitric monoxide metabolite in the same manner as described above and then with the compound of formula (1). Also in this case, unreacted materials and the like are removed using an ultrafiltration membrane in the same manner as described above. Thereafter, the product may be freeze-dried to make it into powder as occasion demands.

The aforementioned precursor modified compound or preliminary precursor modified compound is obtained by carrying out the reaction in accordance with a known method (e.g., JP-B-6-76333 or JP-B-5-64128).

The ratio of the polyoxyalkylene derivative of formula (1) to hemoglobin at the time of their reaction cannot always be specified, because it varies depending on the structure and intended molecular weight of the polyoxyalkylene derivative, but is generally from 0.5 to 70 moles, preferably from 1 to 20 moles, based on 1 mole of hemoglobin.

The nitric monoxide metabolite-polyoxyalkylene-hemoglobin complex (modified hemoglobin compound of interest) of the present invention shows no reduction of the oxygen carrying ability of hemoglobin, has improved safety and does not cause its leakage from the renal glomerulus or vascular endothelium, due to increased molecular weight of hemoglobin to a certain level or more effected by the binding of a polyoxyalkylene thereto, and also does not cause problems such as hypertension at the time of its injection into the living body, due to the binding of a specified amount of a nitric monoxide metabolite, so that it can be used in erythrocyte substitution blood transfusion or organ perfusion simply and easily and also safely.

The following illustratively describes the present invention with reference to production, inventive and comparative examples. However, the present invention is not restricted by these examples.

PRODUCTION EXAMPLE 1

A four neck flask equipped with a nitrogen blowing tube, a stirrer, a thermometer and a condenser/water measuring tube was charged with 85 g of polyethylene glycol #6000 (manufactured by NOF Corporation; molecular weight, 8,500 daltons), 100 ml of toluene and 0.2 g of sodium acetate, and the contents were heated to 80° C. and stirred until they were completely dissolved. Next, while blowing nitrogen gas, the resulting solution was slowly heated until the solvent (toluene) started to reflux and the reflux was continued as such for 1 hour. Thereafter, the water condensed in the water measuring tube was discarded, the water measuring tube was disconnected from the four neck flask and then the condenser tube was again attached to the flask.

Next, the reaction solution was mixed with 2.4 g of succinic anhydride and stirred at 105° C. for 3 hours. Subsequently, unreacted succinic anhydride and toluene were evaporated under a reduced pressure of 100 mmHg or less. After cooling the resulting residue to 80° C., excess sodium acetate was removed by filtration under a reduced pressure to obtain 78 g of polyethylene glycol disuccinate.

The thus obtained polyethylene glycol disuccinate showed an acid value of 12.9 and a saponification number of 26.1.

Next, 17.4 g of polyethylene glycol disuccinate and 200 ml of dimethylformamide were put into a conical flask with ground stopper and heated to 40° C. while stirring with a magnetic stirrer. A 0.98 g portion of dicyclohexylcarbodiimide and 0.56 g of N-hydroxysuccinimide were put into the flask, and the resulting mixture was stirred for 12 hours. Thereafter, the reaction mixture was added dropwise to 1 liter of diethyl ether while stirring, and the thus precipitated crystals were collected by compression filtration to obtain 16.5 g of the activated ester of polyethylene glycol #6000 as white crystals.

Structural formula of the thus obtained compound is shown in Table 1.

TABLE 1

| Structural formula |
|---|
| Production Example 1 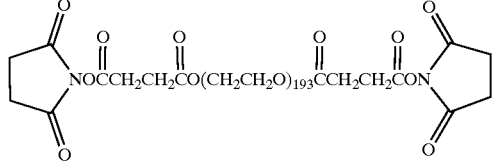 |
| Production Example 2 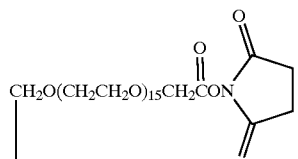 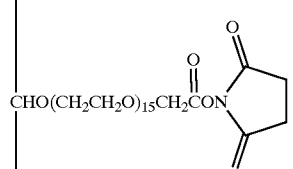 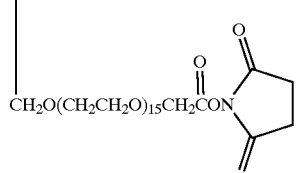 |

TABLE 1-continued

| Structural formula |
|---|
| Production Example 3 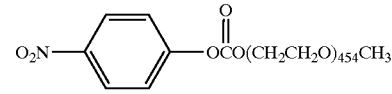 |

PRODUCTION EXAMPLE 2

A 1,000 g portion of polyoxyethylene glyceryl ether (Uniox G-2000 manufactured by NOF Corporation; molecular weight, 2,000 daltons) was put into a five liter capacity autoclave equipped with a stirrer, a thermometer and a nitrogen blowing tube and heated to 60° C. Next, this was mixed with 90 g of sodium methylate, and de-methanol reaction was carried out at 100° C. for 3 hours under a reduced pressure of 100 mmHg or less. The temperature was increased to 115° C., and 252 g of methyl monobromoacetate was gradually forced into the autoclave through a dropping vessel. After completion of the forced charging, the contents were stirred for additional 5 hours at the same temperature.

Thereafter, the reaction mixture was cooled to 30° C., mixed with 200 g of 30% potassium hydroxide aqueous solution, again heated to 80° C. and then stirred for 5 hours to carry out saponification reaction.

After completion of the saponification reaction, entire portion of the reaction solution was transferred into a four neck flask and adjusted to pH 2 using 17.5% hydrochloric acid while stirring. Next, the thus formed carboxylic acid-terminal derivative of polyethylene glycol monoglyceryl ether was extracted three times with one liter of chloroform. The resulting chloroform layers were concentrated to dryness using an evaporator to obtain 982 g of the derivative.

A 26 g portion of the thus obtained derivative was dissolved in 200 g of water and applied to an anion exchange resin Bio-Rad AGIX2 (Bio-Rad Laboratories, USA), thereby once allowing the resin to adsorb the carboxylic acid-terminal derivative, unabsorbed impurities such as unreacted polyethylene glycol monoglyceryl ether were washed out with ion exchange water and then the absorbed matter was eluted with one liter of 0.05 N hydrochloric acid. A 230 g portion of sodium chloride and one liter of chloroform were added to the eluate, and the formed product was again extracted into chloroform layer. The resulting chloroform layer was concentrated to dryness using an evaporator to obtain 22.1 g of purified carboxylic acid-terminal derivative. The thus obtained carboxylic acid-terminal derivative showed an acid value of 81.3.

Thereafter, the terminal carboxylic acid was converted into active ester using dicyclohexylcarbodiimide and N-hydroxysuccinimide in the same manner as described in Production Example 1.

Structural formula of the thus obtained compound is shown in Table 1.

PRODUCTION EXAMPLE 3

A 20 g portion of methoxypolyethylene glycol (molecular weight, 20,000 daltons) was dissolved in 100 ml of chloroform, and the solution was mixed with 10 ml of pyridine and 0.3 g of p-nitrophenyl chloroformate to carry out 5 hours of the reaction at room temperature. Thereafter, the reaction solution was added dropwise to one liter of diethyl ether which was stirred, and the thus precipitated crystals were collected by filtration and dried in a desiccator to obtain 19.8 g of methoxypolyethylene glycol mono-p-nitrophenylformate.

Structural formula of the thus obtained compound is shown in Table 1.

INVENTIVE EXAMPLE 1

A 100 ml portion of erythrocytes of expired blood for transfusion use were suspended in 100 ml of 0.9% sodium chloride aqueous solution and washed four times at 4° C. using a centrifuge. A 60 ml portion of the washed human erythrocytes were subjected to hemolysis using 180 ml of water for injection use, and the membrane components were removed using a filter having a pore size of 0.22 $\mu$m (Millipore Co., USA). The membrane components still remained were removed by one hour of centrifugation at 6,000 rpm.

A 3.29 g (0.051 mmol) portion of the thus obtained human hemoglobin was dissolved in 1,000 ml of 0.1 M phosphate buffer (pH 8.6), and the solution was mixed with 4.54 g (0.51 mmol) of the activated polyoxyethylene produced in Production Example 1 to carry out 2 hours of the reaction at 4° C. by reducing the partial pressure of oxygen to 1 mmHg with argon, thereby obtaining a polyoxyethylene-hemoglobin complex (so-called precursor modified compound).

Next, the reaction solution of precursor modified compound was mixed with 1 mM of EDTA (ethylenediaminetetraacetic acid) and 0.5 mM of DTPA (diethylenetriaminepentaacetic acid) and then adjusted to pH 8.6 with disodium hydrogenphosphate. This was then mixed with 85.7 mg (0.255 mmol) of s-nitrosoglutathione (nitric monoxide metabolite) to carry out 12 hours of the reaction at 4° C.

After the reaction, the reaction solution was applied to an ultrafiltration membrane having a molecular weight cutoff of 30,000 daltons (PM 30, manufactured by Amicon), and purification was repeated until unreacted polyethylene glycol derivative was decreased to 100 ppm or less.

Next, the thus obtained reaction solution was freeze-dried to obtain 5.95 g of an s-nitrosoglutathione-polyoxyethylene-hemoglobin complex (so-called modified hemoglobin compound of interest) as a compound of the present invention.

A result of gel permeation chromatography of the thus obtained compound is shown in FIG. 1.

Measuring conditions of the gel permeation chromatography are as follows.

Column: Toso SW4000XL
Developing solution: 50 mM NP, 0.2 M NaCl, pH 6.8
Flow rate: 0.8 ml/min
Sample injection: 5 $\mu$l (0.5%)
Measuring absorbance: 420 nm It is evident from FIG. 1 that the thus obtained product does not contain unreacted hemoglobin and unreacted polyoxyethylene used as the materials.

The thus obtained s-nitrosoglutathione-polyoxyethylene-hemoglobin complex (modified compound) was found to have a molecular weight of 870,000 daltons.

Also, met-form formation (oxidation of hemoglobin) ratio in the thus obtained compound of the present invention was found to be 1.2%.

The methemoglobin content was measured by a cyanide met-form formation method. Illustratively, each of the hemoglobin samples is diluted to 4 ml with 0.1 M phosphate buffer (pH 6.8) containing 1% Triton X (manufactured by Aldrich) and dispensed into two spectroscopic cells. The sample in one of the cells is measured for its absorbance at 630 nm ($\lambda$M1) and then mixed with 10 $\mu$l of 8% potassium cyanide to measure the absorbance in the same manner ($\lambda$M2). The sample in the other cell is mixed with 10 $\mu$l of 8% potassium ferricyanide to measure the absorbance ($\lambda$T1) and then mixed with the same volume of 8% potassium cyanide to measure the absorbance in the same manner ($\lambda$T2).

The met-form formation ratio was calculated based on a formula ($\lambda$M1–$\lambda$M2)/($\lambda$T1–$\lambda$T2).

Measurement of the s-nitrosoglutathione-polyoxyethylene-hemoglobin complex was carried out using a gel permeation chromatography-aided method (Akaike T. et al., Nanomolar quantification and identification of various nitrosothiols by high performance liquid chromatography coupled with flow reactors of metals and Griess reagent, *J. Biochem.*, 122, 459–466, 1997). Illustrative measuring conditions are as follows.

Column: Eicom GFC-200
Developing solution: 10 mM acetate buffer (pH 5.5) containing 0.1 mM EDTA
First reaction solution: 1.75 mM mercury chloride solution in the above developing solution which does not contain EDTA
Column after first reaction: Eicom CA-ODS
Second reaction solution: 1% sulfanilamide/0.1% N-naphthyl ethylenediamine/2% phosphoric acid (Griess reaction solution)
Measurement: absorbance at 540 nm
Sample injection: 5 $\mu$l By measuring nitrite ion as a standard substance in the same manner, the amount of s-nitrosoglutathione (nitric monoxide metabolite)-hemoglobin complex was calculated from chromatography integration value, and the ratio of s-nitrosoglutathione (nitric monoxide metabolite) introduced into hemoglobin was calculated from the number of injected hemoglobin molecules.

Figure 2:
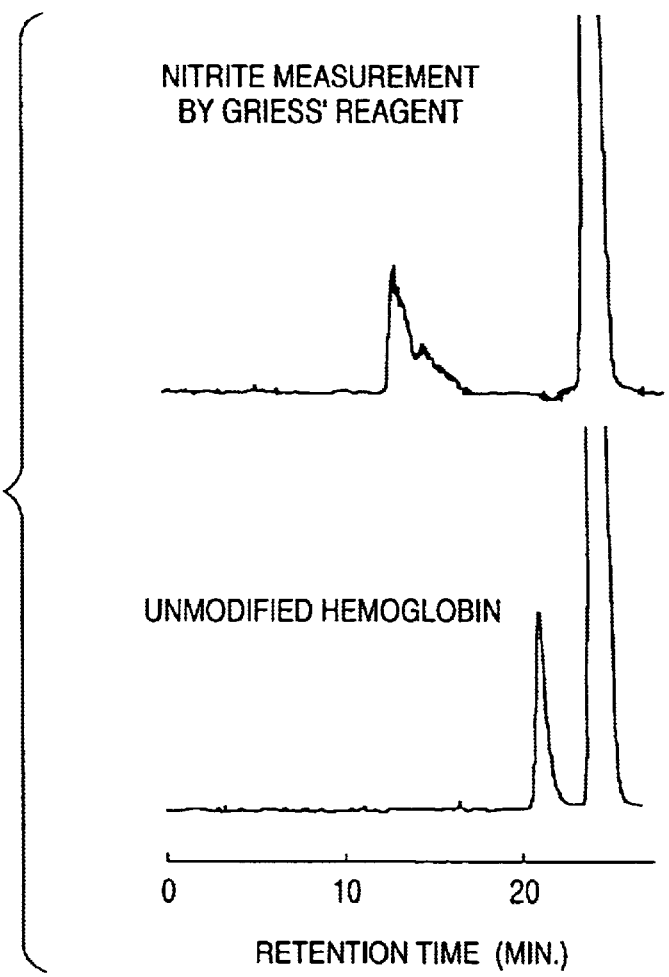
FIG. 2 is a graph showing a result of the measurement of the ratio of s-nitrosoglutathione introduced into the s-nitrosoglutathione-polyoxyethylene-hemoglobin complex obtained in Inventive Example 1.

As shown in FIG. 2, the ratio of s-nitrosoglutathione (nitric monoxide metabolite) introduced into the thus obtained compound of the present invention was 48%.

The number of reactive amino groups was measured by titration with trinitrobenzenesulfonic acid (A. F. S. A. Habeeb, Determination of free amino groups in proteins by trinitrobenzenesulfonic acid, *Anal. Biochem.*, 14, 328–336, 1966), and the modification ratio was determined by comparing the values before and after the modification using the polyoxyalkylene derivative.

Calculation formula of the modification ratio is as follows. Modification ratio=100×(1–the number of residual amino groups after modification/the number of amino groups before modification)

As a result of the measurement in this example, the modification ratio was calculated to be 18.8%, which showed that the compound of Production Example 1 (activated polyoxyethylene) was bound to 9.02 amino groups.

In this connection, the aforementioned hemoglobin solution was prepared in accordance with the method described in JP-B-6-76333.

INVENTIVE EXAMPLE 2

A 50 ml portion of fresh bovine erythrocytes were washed four times at 4° C. with 50 ml of 0.9% sodium chloride aqueous solution using a centrifuge. A 40 ml portion of the thus obtained erythrocyte solution was subjected to hemolysis by adding 80 ml of water for injection use, the lysate was centrifuged at 8,000 rpm for 1 hour and then the membrane components were separated from hemoglobin using an ultrafiltration membrane (cutoff limit, 100,000 daltons).

A 3.87 g (0.06 mmol) portion of the thus obtained hemoglobin was dissolved in 0.1 M phosphate buffer (pH 8.0), and the solution was adjusted to a total volume of 25 ml. After de-oxidation of the solution by vigorous blowing of argon until the partial pressure of oxygen reached 2 mmHg or less, addition of pyridoxal 5'-phosphate was effected in accordance with a known method (R. Benesch et al., *J. Biol. Chem.*, 257 (3), 1320–1324, 1982) to obtain pyridoxal-modified hemoglobin. The thus obtained pyridoxal-modified hemoglobin solution was adjusted to a total volume of one liter by adding 0.1 M borate buffer (pH 8.2).

Next, this solution was mixed with 0.23 g (0.09 mmol) of the activated polyoxyethylene derivative produced in Production Example 2 to carry out 4 hours of the reaction at 2° C. by reducing the partial pressure of oxygen to 1 mmHg with argon, thereby obtaining a polyoxyethylene-pyridoxal-modified hemoglobin complex (so-called preliminary precursor modified compound).

Next, the reaction solution of preliminary precursor modified compound was mixed with 1 mmol of EDTA and 0.5 mmol of DTPA and then adjusted to pH 8.6 with disodium hydrogenphosphate. This was then mixed with 100 mg (0.3 mmol) of s-nitrosoglutathione to carry out 4 hours of the reaction at room temperature, thereby obtaining an s-nitrosoglutathione-polyoxyethylene-hemoglobin complex (so-called precursor modified compound).

This precursor modified compound was further mixed with 24.1 g (1.2 mmol) of the activated polyoxyalkylene derivative produced in Production Example 3, and the reaction was continued for 4 hours at 4° C.

The reaction solution was applied to an ultrafiltration membrane having a molecular weight cutoff of 100,000 daltons (YM100, manufactured by Amicon), and purification was repeated until unreacted polyethylene glycol derivative was decreased to 100 ppm or less.

Next, the thus obtained reaction solution was freeze-dried to obtain 13.8 g of an s-nitrosoglutathione-polyoxyethylene-polyoxyalkylene-hemoglobin complex (so-called modified hemoglobin compound of interest) as a compound of the present invention.

Figure 3:
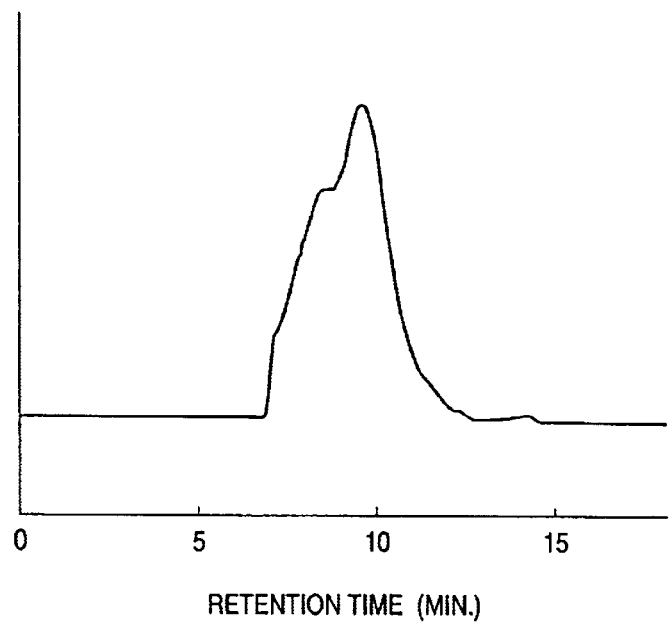
FIG. 3 is a graph showing a result of gel permeation measurement of the s-nitrosoglutathione-polyoxyethylene-hemoglobin complex obtained in Inventive Example 2 using bovine erythrocyte hemoglobin.

A result of gel permeation chromatography of the thus obtained compound is shown in FIG. 3.

Molecular weight of the thus obtained compound of the present invention was 1,670,000 daltons, and the modification ratio of amino groups was 20.1% which showed that the polyoxyalkylene chains were bound to 10.1 amino groups.

Also, the introduced ratio of s-nitrosoglutathione (nitric monoxide metabolite) was found to be 19%.

COMPARATIVE EXAMPLE 1

Synthesis of polyoxyalkylene-hemoglobin complex was carried out in accordance with the method described in JP-B-6-76333.

Firstly, activated ester of polyethylene glycol #4000 (manufactured by NOF Corporation; molecular weight, 3,100 daltons) was synthesized by the same method of Production Example 1.

A four neck flask equipped with a nitrogen blowing tube, a stirrer, a thermometer and a condenser/water measuring tube was charged with 62 g of the just described polyethylene glycol, 100 ml of toluene and 0.2 g of sodium acetate, and the contents were heated to 80° C. and stirred until they were completely dissolved. Next, while blowing nitrogen gas, the resulting solution was slowly heated until the solvent (toluene) started to reflux and the reflux was continued as such for 1 hour. Thereafter, the water condensed in the water measuring tube was discarded, the water measuring tube was disconnected from the four neck flask and then the condenser tube was again attached to the flask.

Next, the reaction solution was mixed with 4.8 g of succinic anhydride and stirred at 105° C. for 3 hours. Subsequently, unreacted succinic anhydride and toluene were evaporated under a reduced pressure of 100 mmHg or less. After cooling the resulting residue to 80° C., excess sodium acetate was removed by filtration under a reduced pressure to obtain 57 g of polyethylene glycol disuccinate.

The thus obtained polyethylene glycol disuccinate showed an acid value of 33.9 and a saponification number of 67.9.

Next, 13.2 g of polyethylene glycol disuccinate and 200 ml of dimethylformamide were put into a conical flask with ground stopper and heated to 40° C. while stirring with a magnetic stirrer. A 1.96 g portion of dicyclohexylcarbodiimide and 1.12 g of N-hydroxysuccinimide were put into the flask, and the resulting mixture was stirred for 12 hours. Thereafter, the reaction mixture was added dropwise to 1 liter of diethyl ether while stirring, and the thus precipitated crystals were collected by compression filtration to obtain 10.8 g of the activated ester of polyethylene glycol #4000 as white crystals.

A 5.16 g (0.08 mmol) portion of membrane component-removed bovine hemoglobin prepared by the same method of Inventive Example 2 was dissolved in 200ml of 0.1 M borate buffer (pH 7.0), the resulting solution was mixed with 6.5 g (1.84 mmol) of the activated ester of polyethylene glycol #4000 and 113 mg (0.773 mmol) of lysine and then the reaction was carried out at 4° C. for 2 hours after reducing the partial pressure of oxygen to 2 mmHg with argon.

The reaction solution was applied to an ultrafiltration membrane having a molecular weight cutoff of 100,000 daltons (YM100, manufactured by Amicon), and purification was repeated until unreacted polyethylene glycol derivative was decreased to 100 ppm or less.

Thereafter, the thus obtained reaction solution was freeze-dried to obtain 6.46 g of the compound of interest.

Molecular weight of the thus obtained compound was 89,000 daltons, and the modification ratio of amino groups was 12.6% which showed that the polyoxyalkylene chains were bound to 6.3 amino groups. COMPARATIVE EXAMPLE 2

Synthesis of a nitric monoxide metabolite-hemoglobin complex was carried out as a comparative test.

Firstly, a pyridoxal-modified hemoglobin solution was obtained in the same manner as described in Inventive Example 2.

A 50 ml portion of fresh bovine erythrocytes were washed four times at 4° C. with 50 ml of 0.9% sodium chloride aqueous solution using a centrifuge. A 40 ml portion of the thus obtained erythrocyte solution was subjected to hemolysis by adding 80 ml of water for injection use, the lysate was centrifuged at 8,000 rpm for 1 hour and then the membrane components were separated from hemoglobin using an ultrafiltration membrane (cutoff limit, 100,000 daltons).

A 3.87 g (0.06 mmol) portion of the thus obtained hemoglobin was dissolved in 0.1 M phosphate buffer (pH 8.0), and the solution was adjusted to a total volume of 25 ml. After de-oxidation of the solution by vigorous blowing of argon until the partial pressure of oxygen reached 2 mmHg or less, addition of pyridoxal 5'-phosphate was effected in accordance with a known method (R. Benesch et al., *J. Biol. Chem.*, 257 (3), 1320–1324, 1982) to obtain pyridoxal-modified hemoglobin. The thus obtained pyridoxal-modified hemoglobin solution was adjusted to a total volume of one liter by adding 0.1 M borate buffer (pH 8.2).

Next, the reaction solution was mixed with 1 mmol of EDTA and 0.5 mmol of DTPA and then adjusted to pH 8.6 with disodium hydrogenphosphate. This was then mixed with 100 mg (0.3 mmol) of s-nitrosoglutathione to carry out 4 hours of the reaction at room temperature.

The thus obtained reaction solution was purified using an ultrafiltration membrane having a molecular weight cutoff of 30,000 daltons (PM30, manufactured by Amicon) until unreacted s-nitrosoglutathione was decreased to 5 ppm or less.

Thereafter, the thus obtained reaction solution was freeze-dried to obtain 2.6 g of the compound of interest.

INVENTIVE EXAMPLE 3

Each of the compounds obtained in Inventive Examples 1 and 2 and Comparative Examples 1 and 2 was dissolved in physiological saline to a concentration of 5% and administered to Wistar rats (7 to 8 weeks of age, 240 to 280 g in body weight) by intravenous injection with a dose of 2.5 ml/kg.

The blood pressure increasing ratio after injection of each compound is shown in Table 2.

TABLE 2

|  | Inventive Example 1 | Inventive Example 2 | Comparative Example 1 | Comparative Example 2 |
|---|---|---|---|---|
| Blood pressure increasing ratio | 5.1% | 6.2% | 26.5% | 5.6% |

INVENTIVE EXAMPLE 4

Figure 4:
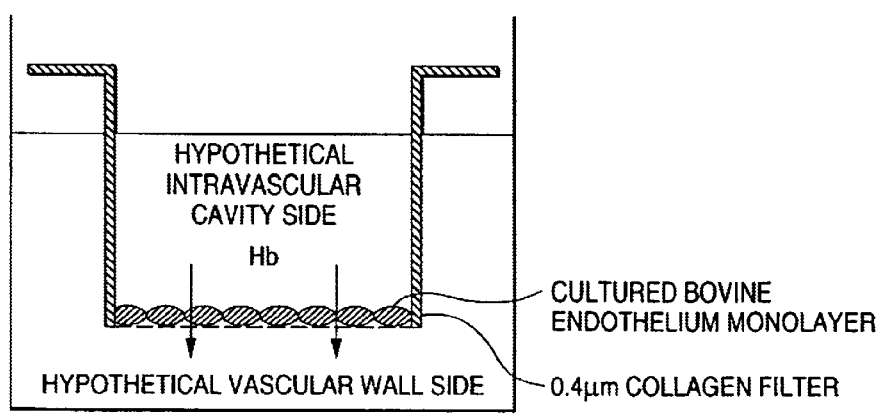
FIG. 4 is a schematic illustration showing the permeability measuring method using cultured bovine endothelium monolayer, used in Inventive Example 4.

Permeability of each of the compounds obtained in Inventive Examples 1 and 2 and Comparative Examples 1 and 2 through vascular endothelial cells was measured by the following model experiment. FIG. 4 is a schematic illustration showing the permeability measuring method.

Bovine aorta endothelial cells were monolayer-cultured on a collagen filter having a pore size of 0.4 μm (Transwell-collagen, manufactured by Corning Coaster) and, using the resulting upper layer as a hypothetical intravascular cavity and the lower layer as a hypothetical vascular wall side, each of the compounds obtained in Inventive Examples 1 and 2 and Comparative Examples 1 and 2 was labeled with $^{125}$I and added to the cavity side with a hemoglobin concentration of 15.5 μM. One hour thereafter, amount of the hemoglobin complex transferred into the lower layer was measured by a gamma counter to calculate the permeability (×10$^{-6}$ cm/sec).

The results are shown in Table 3.

TABLE 3

|  | Inventive Example 1 | Inventive Example 2 | Comparative Example 1 | Comparative Example 2 |
|---|---|---|---|---|
| Permeability (10$^{-6}$ cm/sec) | 0.32 | 0.18 | 2.02 | 6.11 |

What is claimed is:

1. A nitric monoxide metabolite-polyoxyalkylene-hemoglobin complex having a molecular weight of from 100,000 to 2,000,000 daltons, in which a polyoxyalkylene derivative is bound to from 10 to 30% in total of bindable amino groups in hemoglobin and a nitric monoxide metabolite is bound to from 10 to 100% in total of thiol groups of cysteine residues.

2. The nitric monoxide metabolite-polyoxyalkylene-hemoglobin complex according to claim 1, wherein the polyoxyalkylene derivative is represented by a compound of formula (1):

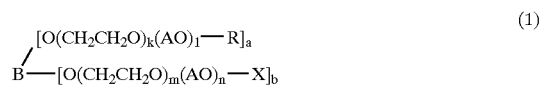

wherein B represents residue of a compound having from 2 to 6 hydroxyl groups, AO represents an oxyalkylene group having 3 or 4 carbon atoms, R represents a hydrocarbon group having from 1 to 30 carbon atoms or a hydroxyl group, k and m are numbers which satisfy $0 \leq k \leq 500$ and $0 \leq m \leq 500$, respectively, and also $20 \leq k+m \leq 1000$, as the average addition mol number of oxyethylene groups, l and n are numbers which satisfy $0 \leq l \leq 10$ and $0 \leq n \leq 10$, respectively, and also $0 \leq l+n \leq 10$, as the average addition mol number of oxyalkylene groups, a and b are numbers which satisfy $0 \leq a \leq 6$ and $1 \leq b \leq 6$, respectively, and also $2 \leq a+b \leq 6$, and X represents a functional group capable of binding to the amino group shown by formula (2), (3), (4) or (5);

wherein c is a number of from 0 to 2 and Y represents hydrogen or p-nitrophenyl group or N-hydroxysuccinimide residue,

wherein d is a number of from 2 to 6 and Y represents hydrogen or N-hydroxysuccinimide residue,

wherein e is 1 or 2, and

wherein Z represents imidazole group.

3. The nitric monoxide metabolite-polyoxyalkylene-hemoglobin complex according to claim 1, wherein the nitric monoxide metabolite is an s-nitroso-low molecular weight thiol compound.

4. The nitric monoxide metabolite-polyoxyalkylene-hemoglobin complex according to claim 2, wherein the nitric monoxide metabolite is an s-nitroso-low molecular weight thiol compound.

5. The nitric monoxide metabolite-polyoxyalkylene-hemoglobin complex according to claim 1, wherein the nitric monoxide metabolite is s-nitrosoglutathione.

6. The nitric monoxide metabolite-polyoxyalkylene-hemoglobin complex according to claim 2, wherein the nitric monoxide metabolite is s-nitrosoglutathione.

7. An oxygen carrier solution which comprises the nitric monoxide metabolite-polyoxyalkylene-hemoglobin complex according to claim 1 in an amount of from 10 g/L to 200 g/L.

8. A method for producing a nitric monoxide metabolite-polyoxyalkylene-hemoglobin complex having a molecular weight of from 100,000 to 2,000,000 daltons, in which a polyoxyalkylene derivative is bound to from 10 to 30% in total of bindable amino groups in hemoglobin and a nitric monoxide metabolite is bound to from 10 to 100% in total of thiol groups of cysteine residues, which comprises allowing a polyoxyalkylene-hemoglobin complex to react with a nitric monoxide metabolite.

9. A method for producing a nitric monoxide metabolite-polyoxyalkylene-hemoglobin complex having a molecular weight of from 100,000 to 2,000,000 daltons, in which a polyoxyalkylene derivative is bound to from 10 to 30% in total of bindable amino groups in hemoglobin and a nitric monoxide metabolite is bound to from 10 to 100% in total of thiol groups of cysteine residues, which comprises allowing a polyoxyalkylene-hemoglobin complex to react with a nitric monoxide metabolite and then with a polyoxyalkylene derivative.

* * * * *